(12) United States Patent
Johns et al.

(10) Patent No.: US 12,042,566 B2
(45) Date of Patent: Jul. 23, 2024

(54) FORMULATIONS OF HOMOTAURINES AND SALTS THEREOF

(71) Applicant: Confluence Pharmaceuticals, LLC, Carmel, IN (US)

(72) Inventors: Steven Johns, Carmel, IN (US); Kenneth Payie, Poway, CA (US); Badrinath Doniparthi, Bengaluru (IN)

(73) Assignee: CONFLUENCE PHARMACEUTICALS, LLC, Carmel, IN (US)

( * ) Notice: Subject to any disclaimer, the term of this patent is extended or adjusted under 35 U.S.C. 154(b) by 473 days.

(21) Appl. No.: 16/612,877

(22) PCT Filed: May 17, 2018

(86) PCT No.: PCT/US2018/033205
§ 371 (c)(1),
(2) Date: Nov. 12, 2019

(87) PCT Pub. No.: WO2018/213589
PCT Pub. Date: Nov. 22, 2018

(65) Prior Publication Data
US 2020/0163895 A1  May 28, 2020

Related U.S. Application Data

(60) Provisional application No. 62/507,532, filed on May 17, 2017, provisional application No. 62/660,690, filed on Apr. 20, 2018.

(51) Int. Cl.
*A61K 9/50* (2006.01)
*A61K 9/00* (2006.01)
*A61K 31/185* (2006.01)

(52) U.S. Cl.
CPC .......... *A61K 9/5073* (2013.01); *A61K 9/0053* (2013.01); *A61K 9/5026* (2013.01); *A61K 9/5042* (2013.01); *A61K 9/5089* (2013.01); *A61K 31/185* (2013.01)

(58) Field of Classification Search
CPC .... A61K 31/185; A61K 9/0056; A61K 9/009; A61K 9/4808; A61K 9/4866; A61K 9/5026; A61K 9/5047; A61K 9/5073; A61K 47/10; A61K 9/0065; A61K 9/2027; A61K 9/2031; A61K 9/2054; A61K 45/06; A61K 9/20; A61K 31/166; A61K 47/32; A61K 31/137; A61K 2300/00; A61K 31/135; A61K 31/138; A61K 31/15; A61K 31/164; A61K 31/165; A61K 31/343; A61K 31/381; A61K 31/385; A61K 31/4515; A61K 31/4525; A61K 31/454; A61K 31/496; A61K 31/519; A61K 31/5377; A61K 31/5415; A61K 31/55; A61K 31/551; A61K 31/553; A61K 31/554; A61K 47/22; A61K 47/38; A61K 9/0002; A61K 9/0004; A61K 9/48; A61K 9/209; A61K 31/40; A61K 31/517; A61K 47/12; A61K 9/2072; A61K 9/2077; A61K 31/16; A61K 31/167; A61K 47/30; A61K 47/34; A61K 9/2018; A61P 25/28; A61P 1/00; A61P 1/04; A61P 25/32

See application file for complete search history.

(56) References Cited

U.S. PATENT DOCUMENTS

| | | |
|---|---|---|
| 6,426,087 B1 | 7/2002 | Saslawski |
| 2002/0006439 A1 | 1/2002 | Skluzacek |
| 2002/0035145 A1 | 3/2002 | Tsai |
| 2005/0042277 A1 | 2/2005 | Srinivas |
| 2008/0206324 A1 | 8/2008 | Gryczke |
| 2009/0182056 A1 | 7/2009 | Laurin |
| 2010/0216734 A1 | 8/2010 | Barlow |
| 2010/0216805 A1 | 8/2010 | Barlow |
| 2011/0142889 A1 | 6/2011 | Lee |
| 2012/0016036 A1 | 1/2012 | Erickson |
| 2012/0077878 A1* | 3/2012 | Berner ............ A61P 1/00 514/578 |
| 2013/0143867 A1 | 6/2013 | Fogel |
| 2013/0224292 A1 | 8/2013 | Fogel |
| 2014/0378440 A1 | 12/2014 | Cohen |
| 2016/0354335 A1 | 12/2016 | Cohen |

FOREIGN PATENT DOCUMENTS

| | | |
|---|---|---|
| CA | 2504471 | 12/2005 |
| EP | 0453001 | 10/1991 |
| EP | 2727473 | 5/2014 |
| JP | 199224517 | 8/1992 |
| JP | 1992224517 | 8/1992 |
| JP | 2001199878 | 7/2001 |

(Continued)

OTHER PUBLICATIONS

El-Ansary, A., & Al-Ayadhi, L. (2014). GABAergic/glutamatergic imbalance relative to excessive neuroinflammation in autism spectrum disorders. Journal of neuroinflammation, 11(1), 189.
(DOW) Ethocel Premium Polymers For Pharmaceutical Applications. Oct. 1998, pp. 1-9.
PCT Search Report prepared for PCT/US2016/045547, mailed Oct. 26, 2016.
PCT Search Report prepared for PCT/US2016/030725, mailed Aug. 5, 2016.
Material Safety Data Sheet Avicel® PH Microcrystalline Cellulose, FMC BioPolymer, Jan. 31, 2009, 9 pages.
Grados, Marco A., et al. "Glutamate drugs and pharmacogenetics of OCD: a pathway-based exploratory approach." Expert opinion on drug discovery 8.12 (2013): 1515-1527.

(Continued)

*Primary Examiner* — Audrea B Coniglio
(74) *Attorney, Agent, or Firm* — Brannon Sowers & Cracraft PC

(57) ABSTRACT

Orally-administrable, pharmaceutical formulations comprising a plurality of pellets are described herein. The pellets comprise a core, a release coating, and an enteric coating, where the release coating comprises, for example, an HPMC.

20 Claims, 2 Drawing Sheets

(56) References Cited

FOREIGN PATENT DOCUMENTS

| | | |
|---|---|---|
| JP | 2001199878 A | 7/2001 |
| JP | 2002503686 | 2/2002 |
| JP | 2008156374 | 7/2008 |
| JP | 2012517480 | 8/2012 |
| JP | 2012254993 A | 12/2012 |
| JP | 2014508812 | 4/2014 |
| JP | 2014508812 A | 4/2014 |
| JP | 2015131864 A | 7/2015 |
| JP | 2015528504 A | 9/2015 |
| JP | 2018515506 | 6/2018 |
| JP | 2018526345 | 9/2018 |
| WO | 2009004082 | 1/2009 |
| WO | 2010093859 | 8/2010 |
| WO | 2010151284 | 12/2010 |
| WO | 2012129551 | 9/2012 |
| WO | 2014018468 | 1/2014 |
| WO | 2014197744 | 12/2014 |
| WO | 2016179252 | 11/2016 |
| WO | WO2016/179252 A1 * 11/2016 ........... A61K 31/185 |
| WO | 2017024129 | 2/2017 |
| WO | 2018213589 | 11/2018 |

OTHER PUBLICATIONS

Olive, M. Foster, et al. "Glutamatergic medications for the treatment of drug and behavioral addictions." Pharmacology Biochemistry and Behavior 100.4 (2012): 801-810.

"Eudragit", Dec. 2012, Eudragit, pp. 107.

PCT Search Report prepared for PCT/US2018/033205, mailed Aug. 10, 2018.

Wink, L. K., Minshawi, N. F., Shaffer, R. C., Plawecki, M. H., Posey, D. J., Horn, P. S., . . . & Swiezy, N. B. (2017). d-Cycloserine enhances durability of social skills training in autism spectrum disorder. Molecular Autism, 8(1), 2.

Urbano, M., Okwara, L., Manser, P., Hartmann, K., & Deutsch, S. I. (2015). A trial of d-cycloserine to treat the social deficit in older adolescents and young adults with autism spectrum disorders. The Journal of Neuropsychiatry and Clinical Neurosciences, 27(2), 133-138.

Chang et al: "Polymethacrylates" In: "Handbook of Pharmaceutical Excipients", 2009, Pharmaceutical Press, UK, XP055758013, ISBN: 978-0-85369-792-3, pp. 525-533.

Deutsch, S. I., Pepe, G. J., Burket, J. A., Winebarger, E. E., Herndon, A. L., & Benson, A. D. (2012). D-cycloserine improves sociability and spontaneous stereotypic behaviors in 4-week old mice. Brain research, 1439, 96-107.

Posey, D. J., Kem, D. L., Swiezy, N. B., Sweeten, T. L., Wiegand, R. E., & McDougle, C. J. (2004). A pilot study of D-cycloserine in subjects with autistic disorder. American Journal of Psychiatry, 161(11), 2115-2117.

Won, H., Lee, H. R., Gee, H. Y., Mah, W., Kim, J. I., Lee, J., . . . & Kim, E. (2012). Autistic-like social behaviour in Shank2-mutant mice improved by restoring NMDA receptor function. Nature, 486(7402), 261-265.

Dey, N. S., Majumdar, S., & Rao, M. E. B. (2008). Multiparticulate drug delivery systems for controlled release. Tropical journal of pharmaceutical research, 7(3), 1067-1075.

Strickley, R. G., Iwata, Q., Wu, S., & Dahl, T. C. (2008). Pediatric drugs—a review of commercially available oral formulations. Journal of pharmaceutical sciences, 97(5), 1731-1774.

Doeppner, T. R., Pehlke, J. R., Kaltwasser, B., Schlechter, J., Kilic, E., Bähr, M., & Hermann, D. M. (2015). The indirect NMDAR antagonist acamprosate induces postischemic neurologic recovery associated with sustained neuroprotection and neuroregeneration. Journal of Cerebral Blood Flow & Metabolism, 35(12), 2089-2097.

Brunsdon, V. E., Colvert, E., Ames, C., Garnett, T., Gillan, N., Hallett, V., . . . & Happé, F. (2015). Exploring the cognitive features in children with autism spectrum disorder, their co-twins, and typically developing children within a population-based sample. Journal of Child Psychology and Psychiatry, 56(8), 893-902.

Hagerman, R. J., & Polussa, J. (2015). Treatment of the psychiatric problems associated with fragile X syndrome. Current opinion in psychiatry, 28(2), 107.

Urbano, M., Okwara, L., Manser, P., Hartmann, K., Herndon, A., & Deutsch, S. I. (2014). A trial of D-cycloserine to treat stereotypies in older adolescents and young adults with autism spectrum disorder. Clinical neuropharmacology, 37(3), 69.

E. Santini et al., "Consolidation of extinction learning involves transfer from NMDA-independent to NMDA-dependent memory," J Neurosci., 21:9009-9017 (2001).

Rowe, R. C., Sheskey, P. J., & Owen, S. C. (2006). Ethylcellulose. Handbook of Pharmaceutical Excipients. Pharmaceutical press, London, 278-282.

* cited by examiner

FORMULATIONS OF HOMOTAURINES AND SALTS THEREOF

CROSS-REFERENCE TO RELATED APPLICATION

This application is a U.S. national application under 37 C.F.R. § 371(b) of International Application Serial No. PCT/US2018/033205 filed May 17, 2018, which claims the benefit under 35 U.S.C. § 119(e) of U.S. Provisional Application Ser. No. 62/507,532, filed May 17, 2017, and U.S. Provisional Application No. 62/660,690, filed Apr. 20, 2018, the disclosure of each of which is incorporated herein by reference.

TECHNICAL FIELD

The invention described herein relates to sprinkle formulations for use as a medicament. More specifically, the invention described herein relates to pellets comprising a core comprising a homotaurine or derivative or salt thereof, a release coating, and an enteric coating.

BACKGROUND 3-(Acetylamino)propylsulfonic acid, also referred to as N-acetylhomotaurine or acamprosate is a derivative of homotaurine, a naturally occurring structural analog of γ-aminobutyric acid (GABA) that appears to affect multiple receptors in the central nervous system (CNS). As an antiglutamatergic agent, acamprosate has been reported to exert a neuropharmacological effect as an antagonist of N-methyl-D-aspartate (NMDA) receptors. The mechanism of action reportedly includes blocking of the $Ca^{2+}$ channel to slow $Ca^{2+}$ influx and reducing expression of c-fos, leading to changes in messenger RNA transcription and the concomitant modification to the subunit composition of NMDA receptors in selected brain regions (Zornoza et al., *CNS Drug Reviews*, 2003, 9(4), 359-374; and Rammes et al., *Neuropharmacology* 2001, 40, 749-760). There is also evidence that acamprosate may interact with excitatory glutamatergic neurotransmission in general, and as an antagonist of the metabotropic glutamate receptor subtype 5 (mGluR5) in particular (De Witte et al., *CNS Drugs* 2005, 19(6), 517-37). The glutamatergic mechanism of action of acamprosate may explain the effects of acamprosate on alcohol dependence, and suggests other therapeutic activities, such as in neuroprotection.

U.S. Pat. Nos. 6,391,922 and 6,689,816 disclose a treatment for neuropsychiatric disorders, including anxiety disorders, mood disorders, psychotic disorders, somatoform disorders, and neuropsychiatric symptoms resulting from movement disorders. U.S. Pat. No. 7,745,493 discloses a treatment for movement disorders, including tardive dyskinesia, tic disorders, Tourette's syndrome, and blepharospasm, and other focal dystonias. U.S. Pat. No. 8,865,769 discloses combinations and methods for the treatment of neurological disorders related to glutamate excitotoxicity and amyloid toxicity, such as multiple sclerosis, Alzheimer's disease, Alzheimer's disease related disorder, Amyotrophic Lateral Sclerosis, Parkinson's disease, Huntington's disease, neuropathic pain, alcoholic neuropathy, alcoholism or alcohol withdrawal, and spinal cord injury.

Published US Patent application No. 2011/0294879 discloses a treatment for fragile X syndrome, fragile X-associated tremor/ataxia syndrome, and Down's syndrome. WO 2010093859 A1 discloses a treatment for subjects diagnosed with either comorbid or idiopathic autism and fragile x syndrome.

Acamprosate is designated a Class III compound in the Biopharmaceutics Classification System (BCS), a polar molecule having high solubility and low passive permeability across cellular membranes. As a consequence, the oral bioavailability of acamprosate in humans is reportedly only about 11%, and poor absorption of the drug from the GI tract likely contributes to its limited tolerability. An additional consequence is that a relatively large tablet has been required to achieve a therapeutic effect.

Acamprosate calcium, marketed as Campral® by Forest Pharma, was first approved by the FDA in 2004. Campral® is indicated for the maintenance of abstinence from alcohol in patients with alcohol dependence who are abstinent at treatment initiation. Campral® is supplied as an enteric-coated tablet for oral administration. Each Campral® tablet contains acamprosate calcium 333 mg, equivalent to 300 mg of acamprosate. Campral® 333 mg tablets are enteric-coated, white, round, biconvex tablets. The recommended dose of Campral® is two 333 mg tablets (666 mg) taken three times daily. A lower dose may be effective in some patients. Although dosing may be done without regard to meals, dosing with meals was employed during clinical trials and is suggested in those patients who regularly eat three meals daily. As an enteric-coated tablet, any disruption of the coating allows for immediate dissolution of the tablet before moving through the upper digestive tract and into the lower digestive tract for absorption. When the pill's enteric-coating is broken, such as by chewing or cutting, an adverse reaction is observed and GI distress, such as diarrhea, nausea, and vomiting, increases.

Campral® tablets are 10 mm in size, which presents a challenge for both pediatric and adult patients. The FDA has issued draft guidance on size, shape and other physical attributes of generic tablets and capsules which outlines the difficulties swallowing tablets and capsules for many individuals and can lead to a variety of adverse events and patient noncompliance with treatment regimens. www.fda.gov/downloads/drugs/guidancecomplianceregulatory information/guidances/ucm377938.pdf. The guidance estimates over 16 million people in the U.S. have some difficulty swallowing a tablet or capsule. The size and shape of the tablets can affect the transit of the product through the pharynx and esophagus and may directly affect the patient's ability to swallow a product. This transit difficulty can lead to disintegration of the product in the esophagus and the potential for ulceration, stricture or perforation as well as other adverse events like pain, gagging, choking and aspiration. The studies presented by the FDA suggest that tablets larger than 8 mm in diameter are associated with increases in patient complaints and difficulties and increased esophageal transit time.

A clinical study of Campral® in subjects with Fragile X Syndrome (FXS) and comorbid autistic disorder demonstrated significant improvements in communication and social interaction skills. Erickson et al, J. Autism Dev. Disord. (2010). However, gastrointestinal distress (nausea and vomiting) were commonly observed side effects in the majority of Fragile X subjects treated in this study. In addition, it has been reported that between 40%-90% of pediatric patients with Fragile X Syndrome (n=1,361 FXS patients) had significant difficulty swallowing a whole solid pill. Bailey D. B., et. al. Medication Untilization for Targeted Symptoms in Children and Adults with Fragile X Syndrome: US Survey. J Dev Behav Pediatr. 2012 33:62-69.

That difficulty has been reported to be a barrier to recruiting patients for open-label pilot studies with Campral®.

There is yet a long-felt and unmet need for oral formulations of acamprosate which do not induce gastrointestinal problems to treat patients who are unable or unlikely to swallow tablet or capsule formulations of the drug. There is also a long-felt and unmet need for oral formulations of acamprosate that provide a sustained and consistent exposure over extended periods of time between dosing, such as 3 h, 4 h, 5 h, 6 h, or greater.

SUMMARY OF THE INVENTION

Figure 1:
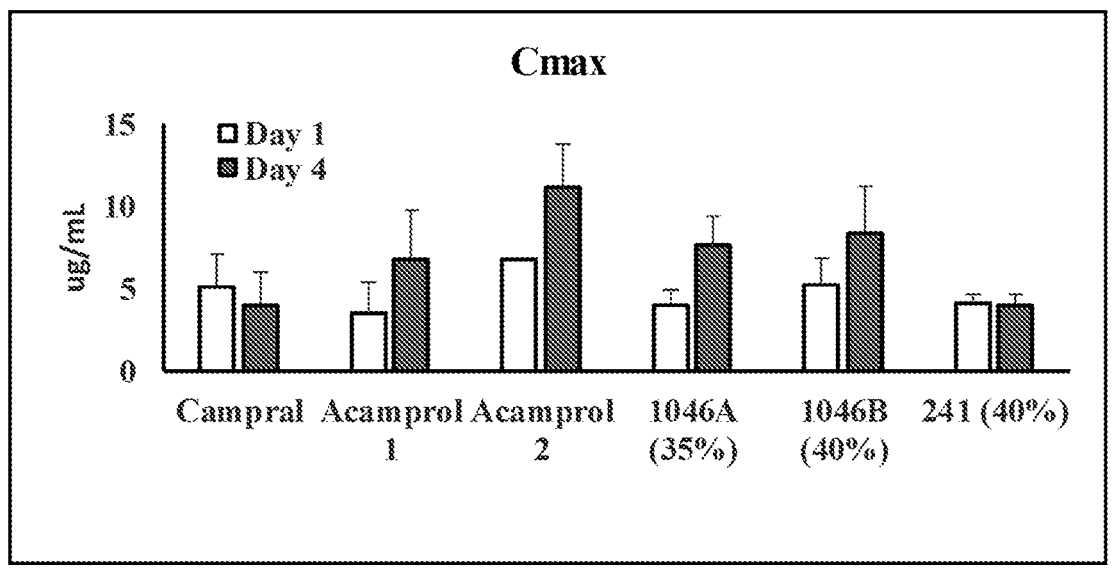
FIG. 1 shows the $C_{max}$ in dogs for formulations described herein compared against Reference tablets for dosing Days 1 and 4. Dosing for each formulation was normalized to 2×333 mg acamprosate calcium, BID for each example. There were not any observed statistical differences between any of the tested formulations on Day 4.

Orally-administrable, sprinkle formulations comprising a plurality of acamprosate containing pellets is described herein. It has been unexpectedly discovered that pellets described herein exhibit improved pharmacokinetic parameters over conventional formulations, including Camprol® and Acamprol® tablets, and other reported sprinkle formulations.

The pellets described herein comprise a core, a release coating, and an enteric coating, and optional additional coatings.

The core comprises a homotaurine or derivative thereof, such as an acamprosate, as the active pharmaceutical ingredient (API), and optionally a diluent. The release coating comprises, consists essentially of, or consists of a thermoplastic cellulose ether other than an ethyl cellulose (EC), such as an hydroxypropyl methylcellulose (HPMC), or a mixture of a thermoplastic cellulose ether, such as an HPMC and an EC. It is to be understood that the HPMC and HPMC-EC mixtures provide a release coating to the core, as defined herein. Accordingly, it is to be understood that release coatings that consist essentially of HPMC or an HPMC-EC mixture do not include other components that are well-established to provide release characteristics, or that would substantially alter the release characteristics of the HPMC or an HPMC-EC mixture. However, it is also to be understood that any number of additional components may be included in release coatings that consist essentially of HPMC or an HPMC-EC mixture where those additional components are not well-established or well-recognized to provide release characteristics, or that would not substantially alter the release characteristics of the HPMC or an HPMC-EC mixture.

As used herein with other aspects of the invention, the transitional phase consisting essentially of will have the corresponding parallel meaning.

It is to be understood that any conventional enteric coating may be included in the sprinkle formulations described herein. Illustratively, the enteric coating comprises a polymer of a methacrylic acid or any derivative thereof, or a combination of the foregoing.

DETAILED DESCRIPTION

In one illustrative embodiment of the invention described herein, the active ingredient is a homotaurine or derivative thereof, such as an acetylaminopropane sulfonate, an acetylaminopropane sulfonate salt, taltrimide, tauromustine, and the like. In another embodiment, the active ingredient is 3-acetamidopropane-1-sulfonic acid (also referred to as N-acetyl homotaurine, or acamprosate) or a pharmaceutically acceptable salt thereof. In another embodiment, the active ingredient is acamprosate calcium. It is to be understood that any form of the active ingredient may be used or incorporated into the sprinkle formulations described herein. For example, formulations are described herein that comprise, consist essentially of, or consist of Form B of acamprosate calcium. In addition, formulations are described herein that comprise, consist essentially of, or consist of acamprosate calcium, but are substantially free of, or completely free of, Form B.

Several illustrative embodiments of the invention are described by the following clauses:

Described herein are sprinkle formulations that include a plurality of pellets, where the pellets comprise a core, a release coating, and an enteric coating.

The pellets of the preceding clause wherein the core comprises acamprosate calcium, and optionally one or more diluents.

the pellets of any one of the preceding clauses wherein the diluent comprises acacia, gelatin, hydroxypropyl cellulose, hydroxypropylmethyl cellulose, methylcellulose, polyethylene glycol (PEG), povidone, sucrose, starch, or any combination of the foregoing.

The pellets of any one of the preceding clauses wherein the diluent comprises, consists essentially of, or consists of a microcrystalline cellulose (MCC) or a cellulose gel, such as Avicel PH101.

The pellets of any one of the preceding clauses wherein the core comprises about 30% to about 80%, about 30% to about 75%, about 30% to about 70%, about 30% to about 65%, or about 30% to about 60% acamprosate calcium by weight.

The pellets of any one of the preceding clauses wherein the core comprises about 40% to about 80%, about 40% to about 75%, about 40% to about 70%, about 40% to about 65%, or about 40% to about 60% acamprosate calcium by weight.

The pellets of any one of the preceding clauses wherein the core comprises about 50% to about 90%, about 50% to about 85%, about 50% to about 80%, about 50% to about 75%, about 50% to about 70%, about 50% to about 65%, or about 50% to about 60% acamprosate calcium by weight.

The pellets of any one of the preceding clauses wherein the core comprises about 60% to about 90%, about 60% to about 85%, about 60% to about 80%, about 60% to about 75%, about 60% to about 70%, or about 60% to about 65% acamprosate calcium by weight.

The pellets of any one of the preceding clauses wherein the release coating comprises a thermoplastic cellulose ether other than EC, or a mixture of one or more thermoplastic cellulose ethers and EC.

The pellets of any one of the preceding clauses wherein the release coating comprises, consists essentially of, or consists of an HPMC, or a mixture of HPMC and an EC. Illustrative ECs include, but are not limited to Ethyl cellulose 10 standard, Ethyl cellulose 20 standard, and combinations thereof.

The pellets of any one of the preceding clauses wherein the release coating comprises, consists essentially of, or consists of an HPMC, and is free of or substantially free of an EC.

The pellets of any one of the preceding clauses wherein the release coating comprises, consists essentially of, or consists of a mixture of HPMC and an EC, where the ratio of HPMC to EC is about 4.5 to about 0.5, about 4 to about 1, about 3.5 to about 1.5; about 3 to about 2, or about 2.5 by weight.

The pellets of any one of the preceding clauses wherein the release coating comprises, consists essentially of, or consists of a mixture of HPMC and an EC, where the ratio of HPMC to EC is about 5 to about 1, about 4.5 to about 1, about 4 to about 1, about 3.5 to about 1; about 3 to about 1, about 2.5 to about 1, about 2 to about 1, or about 1.5 to about 1 by weight.

The pellets of any one of the preceding clauses wherein the release coating comprises, consists essentially of, or consists of a mixture of HPMC and an EC where the ratio of HPMC to EC is about 1 or greater by weight.

The pellets of any one of the preceding clauses wherein the release coating comprises, consists essentially of, or consists of a mixture of HPMC and an EC where the ratio of HPMC to EC is greater than 1 by weight.

The pellets of any one of the preceding clauses wherein the release coating further comprises one or more excipients, such as emulsifiers, carnauba wax, shellac, and the like, and any combination of the foregoing.

The pellets of any one of the preceding clauses wherein the release coating further comprises a citrate ester, such as but not limited to triethyl citrate, triethyl citrate and the related esters acetyl triethyl citrate, tributyl citrate, and acetyl tributyl citrate, and combinations thereof.

The pellets of any one of the preceding clauses wherein the HPMC or mixture of HPMC and an EC is at least about 50%, about 60%, about 65%, about 70%, about 75%, or about 80% of the release coating by weight.

The pellets of any one of the preceding clauses wherein the release coating adds about 5 w/w % to about 30 w/w %, about 5 w/w % to about 25 w/w %, about 5 w/w % to about 20 w/w %, about 5 w/w % to about 15 w/w %, about 5 w/w % to about 10 w/w %, or about 5 w/w % to about 7 w/w % additional weight to the cores. In each such instance herein, the percent weight increase is optionally designated as (+w)/w.

The pellets of any one of the preceding clauses wherein the release coating adds about 3 w/w % to about 15 w/w %, about 3 w/w % to about 12 w/w %, about 3 w/w % to about 10 w/w %, or about 3 w/w % to about 7 w/w % additional weight to the cores. It is to be understood that the weight difference is applicable to individual cores, a plurality of cores, or as an average over a plurality of cores.

The pellets of any one of the preceding clauses wherein the enteric coating comprises an anionic polymer, such as a polymer or copolymer comprising acrylate and/or methacrylate radicals, and esters thereof. Illustratively, the enteric coating is a copolymer of methacrylic acid and methyl methacrylate. Illustratively, the ratio of acid residues to ester residues is in the range from about 1:3 to about 3:1, or about 1:2 to about 1:1.

The pellets of any one of the preceding clauses wherein the enteric coating comprises, consists essentially of, or consists of a Eudragit polymer, including but not limited to a Eudragit S, Eudragit L, such as Eudragit L30 D55 and Eudragit L100 D55, and the like.

The pellets of any one of the preceding clauses wherein the enteric coating further comprises one or more excipients, such as an emulsifier, an anticaking agent, a glidant, and the like.

The pellets of any one of the preceding clauses wherein the enteric coating further comprises a citrate ester, such as but not limited to triethyl citrate, triethyl citrate and the related esters acetyl triethyl citrate, tributyl citrate, and acetyl tributyl citrate, and combinations thereof.

The pellets of any one of the preceding clauses wherein the enteric coating further comprises a talc.

The pellets of any one of the preceding clauses wherein the anionic copolymer is at least about 40%, about 45%, about 50%, about 55%, about 60%, about 65%, or about 70% of the enteric coating by weight.

The pellets of any one of the preceding clauses further comprising a citrate ester and talc, wherein the ratio of citrate ester to talc is about 1 or less, about 0.75 or less, or about 0.5 or less by weight.

The pellets of any one of the preceding clauses wherein the enteric coating adds about 30 w/w % to about 60 w/w %, about 30 w/w % to about 55 w/w %, about 30 w/w % to about 50 w/w %, about 30 w/w % to about 45 w/w %, or about 30 w/w % to about 40 w/w % additional weight to the release coated cores.

The pellets of any one of the preceding clauses wherein the enteric coating adds about 35 w/w % to about 60 w/w %, about 35 w/w % to about 55 w/w %, about 35 w/w % to about 50 w/w %, about 35 w/w % to about 45 w/w % or about 35 w/w % to about 40 w/w % additional weight to the release coated cores.

The pellets of any one of the preceding clauses wherein the enteric coating adds about 40 w/w % to about 60 w/w %, about 40 w/w % to about 55 w/w %, about 40 w/w % to about 50 w/w %, or about 40 w/w % to about 45 w/w % additional weight to the release coated cores. It is to be understood that the weight difference is applicable to individual release coated cores, a plurality of release coated cores, or as an average over a plurality of release coated cores.

The pellets of any one of the preceding clauses comprising at least about 30%, at least about 35%, at least about 40%, at least about 45%, at least about 50%, at least about 55%, or at least about 60% acamprosate calcium by weight.

The pellets of any one of the preceding clauses comprising at least about 35%, at least about 36%, at least about 37%, at least about 38%, at least about 39%, at least about 40%, at least about 41%, at least about 42%, at least about 43%, at least about 44%, or at least about 45% acamprosate calcium by weight.

The pellets of any one of the preceding clauses comprising at least about 0.1%, at least about 1%, at least about 2%, at least about 3%, at least about 4%, at least about 5%, at least about 6%, or at least about 7% HPMC by weight.

The pellets of any one of the preceding clauses comprising at least about 0.5%, at least about 1%, at least about 1.5%, at least about 2%, at least about 2.5%, at least about 3%, at least about 3.5%, at least about 4%, at least about 4.5%, or at least about 5% HPMC by weight.

The pellets of any one of the preceding clauses comprising less than 5%, less than 4%, less than 3%, less than 2%, less than 1.5%, less than 1%, or less than 0.5% EC by weight.

The pellets of any one of the preceding clauses comprising less than 30%, less than 25%, less than 20%, less than 15%, or less than 10% anionic polymer by weight. Illustratively, the anionic polymer is a polymer or copolymer comprising acrylate and/or methacrylate radicals, and esters thereof, such as a Eudragit.

The pellets of any one of the preceding clauses comprising less than 5000 ppm, less than 4000 ppm, less than 3000 ppm, less than 2500 ppm, less than 2000 ppm, less than 1500 ppm, less than 500 ppm, or less than 100 ppm total organic solvent, such as acetone, isopropanol, and the like.

The pellets of any one of the preceding clauses comprising less than 5000 ppm, less than 4000 ppm, less than 3000 ppm, less than 2500 ppm, less than 2000 ppm, less than 1500 ppm, less than 500 ppm, or less than 100 ppm isopropanol.

The pellets of any one of the preceding clauses substantially free of, or free of organic solvent, such as acetone, isopropanol, and the like.

The pellets of any one of the preceding clauses substantially free of, or free of isopropanol or acetone, or both.

It is to be understood that each description herein of a weight percent or weight ratio is applicable to individual pellets as well as pluralities of pellets, where the percent or ratio refers to the average of the plurality of pellets. It is also to be understood that the plurality of pellets can refer to either a bulk sample or an individual dosage unit.

The pellets of any one of the preceding clauses wherein the active ingredient is homogeneously dispersed in the pellets.

The pellets of any one of the preceding clauses wherein the core is substantially smooth in texture.

The pellets of any one of the preceding clauses wherein the core is substantially non-porous.

The pellets of any one of the preceding clauses wherein the core and/or the release coated core is substantially spherical.

In another embodiment, a plurality of pellets is described herein that range in size from about 0.25 to about 3 mm, or about 0.25 to about 2.5 mm, or about 0.25 to about 2 mm, or about 0.25 to about 1.5 mm, or about 0.5 mm to about 3 mm, or about 0.5 to about 2.5 mm, or about 0.5 mm to about 2 mm, or about 0.5 mm to about 1.5 mm. In another embodiment, the majority of pellets in a dosage unit fall within the foregoing ranges. Pellet size may be determined by any conventional method, such as described in Bead Size for Drug Products Labeled for Sprinkle (per the current US-FDA Guidance at http://www.fda.gov/downloads/drugs/_guidancecomplianceregulatory_information/guidances/ucm240243.pdf).

In another embodiment, a plurality of pellets is described herein that range in size from about 0.25 to about 1 mm, or about 0.5 to about 1 mm, about 0.25 to about 0.75 mm, or about 0.5 to about 0.75 mm. In another embodiment, the majority of pellets in a dosage unit fall within the foregoing ranges.

In another embodiment, a plurality of pellets described herein that range in size from about 0.5 mm to about 3 mm, or about 0.5 mm to about 2.5 mm, or about 0.5 to about 2 mm, or about 0.5 mm to about 1.5 mm, where the pellet comprises at least 30%, at least 35%, at least 40%, at least 45%, or at least 50% acamprosate sodium by weight.

In another embodiment, a plurality of pellets described herein that range in size from about 0.25 to about 1 mm, or about 0.5 to about 1 mm, or about 0.5 to about 0.75 mm, where the pellet comprises at least 50%, at least 55%, at least 60%, at least 65%, or at least 70% acamprosate sodium by weight.

It is to be understood that pellet size and drug load may be selected with consideration of the other. For example, smaller pellets or pellet ranges may illustratively have higher drug load than larger pellets or pellet ranges.

In another embodiment, sprinkle formulations are described herein that achieve less than 10%, less than 7%, less than 5%, less than 4%, less than 3%, less than 2%, or less than 1% release of acamprosate at pH 1.2.

In another embodiment, sprinkle formulations are described herein that achieve greater than 70%, greater than 75%, greater than 80%, greater than 85%, or greater than 90% release of acamprosate within 30 minutes in pH 6.8 buffer.

In another embodiment, sprinkle formulations are described herein that achieve greater than 85%, greater than 90%, greater than 92%, greater than 95%, or greater than 97% release of acamprosate within 90 minutes in pH 6.8 buffer.

In another embodiment, sprinkle formulations are described herein that achieve greater than 85%, greater than 90%, greater than 92%, greater than 95%, or greater than 97% release of acamprosate within 60 minutes in pH 6.8 buffer.

It is to be understood that API release is evaluated using any conventional in vitro assay at pH 1.2, and/or in a pH 6.8 buffer.

In another embodiment, the pellets described herein are included in a pharmaceutical sprinkle formulation.

In another embodiment, the plurality of pellets or the pharmaceutical formulation thereof further comprises one or more additives selected from the group consisting of lubricants, colorants, flow agents, glidants, fillers, perfumes, flavors, flavor enhancers, flavor masking agents, or effervescent agents, or any combination of the foregoing.

In another embodiment, the pellets described herein, and the pharmaceutical formulations thereof, are useful in treating diseases.

In another embodiment, the pellets described herein, and the pharmaceutical formulations thereof are useful in the manufacture of medicaments for treating diseases.

In another embodiment, the pellets described herein, and the pharmaceutical formulations thereof are useful in methods for treating diseases, where the methods include administering a composition or dosage unit described herein, illustratively by sprinkling the composition or dosage unit onto or into a food having a pH of about 5.5 or less, where the food is to be ingested. The compositions and dosage units are configured and adapted to be ingested contemporaneously or simultaneously.

In another embodiment, the food is applesauce or yogurt.

In another embodiment, dosage units are described.

In another embodiment, the dosage unit is a plurality of pellets contained in a capsule.

In another embodiment, the dosage unit is a plurality of pellets contained in a sachet, such as aluminum pouches.

In another embodiment, the dosage unit is a plurality of pellets contained in a straw.

In another embodiment, the active ingredient is acamprosate calcium and the unit dose corresponds to about 100 mg to about 2500 mg or acamprosate.

In another embodiment, the unit dose contains about 333 mg acamprosate calcium.

In another embodiment, the unit dose contains about 600, about 400, about 300, or about 200 mg acamprosate calcium.

In another embodiment, the unit dose contains about 600, about 400, about 300, or about 200 mg acamprosate.

In another embodiment, one or more dosage units are administered 1-4 times per day, or 2-3 times per day.

In another embodiment, one or two dosage units are administered 3 times per day.

In another embodiment, one or two dosage units are administered 2 times per day.

It is to be understood that all allowable combinations of the aspects and embodiments described above and elsewhere within this application are further aspects and embodiments off the invention described herein.

"Bioavailability" refers to the rate and amount of a drug that reaches the systemic circulation of a subject following administration of the drug to the subject and can be determined by evaluating, for example, the plasma or blood concentration-versus-time profile for a drug.

"Enteric coating" refers to a polymer barrier applied to or on an oral medication to protect the drug from the lower pH of the stomach, decrease degradation, and/or decrease or prevent premature dissolution. It has been reported that release of acamprosate calcium in the stomach leads to gastrointestinal distress and/or irritation of the stomach.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Salt" refers to a chemical compound consisting of an assembly of cations and anions. Salts of a compound of the present disclosure include stoichiometric and non-stoichiometric forms of the salt. In certain embodiments, because of its potential use in medicine, salts of an active ingredient are pharmaceutically acceptable salts.

"Pharmaceutically acceptable salt" refers to a salt of a compound, which possesses the desired pharmacological activity of the parent compound. When the active ingredient is acamprosate, the salt may be the calcium salt.

"Pharmaceutical composition" refers to at least one active ingredient and at least one pharmaceutically acceptable vehicle with which at least one active ingredient is administered to a subject.

"Sprinkle formulation" refers to enteric-coated beads or pellets which can be ellipsoidal or generally spherical or cylindrical in shape and is currently defined by the FDA to be 0.82 mm to 3.04 mm (+ or −10% variation) in size and can be administered orally with food with or without chewing. Sprinkles can be manufactured in several shapes such as cylindrical, cylindrical with round ends, dumb-bell, ellipsoid or spherical in shape. See "Guidance for Industry Size of Beads in Drug Products Labeled for Sprinkle," U.S. Department of Health and Human Services Food and Drug Administration Center for Drug Evaluation and Research (CDER) May 2012 CMC Rev. 1. It is understood that pellets that are more spherical may have one or more of the following attributes: lower eccentricity, fewer and/or smaller planar regions, fewer and/or lower peaks, points, or prominences, fewer and/or shallower valleys, indentations, or depressions.

"Sachet" is a small flexible package made by bonding, e.g., two layers together on all four sides. In the pharmaceutical arts, the term often refers to single-use, sealed, flexible aluminum pouches which contains a dose of the formulation of which could be presented as a liquid, powder, cream, paste or granule.

"Subject" refers to a mammal, for example, a human.

"Sustained release" or "modified release" refers to release of a compound from a dosage form of a pharmaceutical composition at a rate effective to achieve a therapeutic or prophylactic concentration of the compound, or active metabolite thereof, in the systemic circulation of a subject over a prolonged period of time relative to that achieved by administration of an immediate release formulation of the same compound by the same route of administration. In some embodiments, release of a compound occurs over a time period of at least about 2 hours, at least about 4 hours, at least about 6 hours, at least about 8 hours, at least about 12 hours, and in some embodiments at least about 16 hours, at least about 20 hours, or at least about 24 hours.

"Treating" or "treatment" of any disease refers to arresting or ameliorating a disease or at least one of the clinical symptoms of a disease or disorder, reducing the risk of acquiring a disease or at least one of the clinical symptoms of a disease, reducing the development of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter that may or may not be discernible to the subject. In certain embodiments, "treating" or "treatment" refers to delaying the onset of the disease or at least one or more symptoms thereof in a subject which may be exposed to or predisposed to a disease or disorder even though that subject does not yet experience or display symptoms of the disease.

"Therapeutically effective amount" refers to the amount of a compound that, when administered to a subject for treating a disease, or at least one of the clinical symptoms of a disease, is sufficient to affect such treatment of the disease or symptom thereof. The "therapeutically effective amount" may vary depending, for example, on the compound, the disease and/or symptoms of the disease, severity of the disease and/or symptoms of the disease or disorder, the age, weight, and/or health of the subject to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a subject. A therapeutically effective dose may vary from compound to compound, and from subject to subject, and may depend upon factors such as the condition of the subject and the route of delivery. A therapeutically effective dose may be determined in accordance with routine pharmacological procedures known to those skilled in the art.

In another embodiment, the API compound is homogeneously dispersed in the core of the pellet, which is enclosed by a release coating, and further enclosed by an enteric coating to form a pellet. The enteric coating, which has low solubility at low pH delays the release of API from the pellet until after the pellet has exited the stomach. In the neutral upper intestine, the enteric coating dissolves, exposing the release coating. The release coating slowly dissolves in pH greater than about 5, slowly releasing the API.

The pellets described herein include a release coating comprising HPMC or a mixture of HPMC and EC. It is to be understood that HPMC may also be used as a diluent in the core, as described herein. It has been unexpectedly discovered that release coatings comprising, consisting essentially of, or consisting of HPMC or a mixture of HPMC and EC may provide better PK performance characteristics compared to Camprol® and Acamprol®, and also alternative sprinkle formulations comprising EC release coatings.

It was unexpectedly discovered herein that HPMC and mixtures of HPMC and EC provide for a faster release of the active ingredient in the core compared to EC alone at comparable coating thicknesses at pH 6.8. It is understood that release coating thickness is related to release, where thinner coatings provide more complete release. Nonetheless, it was unexpectedly discovered that release coatings comprising, consisting essentially of, or consisting of HPMC or a mixture of HPMC and EC provide a more complete release compared to EC coatings at comparable thickness, and even EC coatings with thinner thickness.

Without being bound by theory, it is believed herein that a more spherical shape will provide a better release profile, and/or a more consistent release profile over multiple doses, such as a more rapid and/or more complete release at a predetermined pH, such as a pH of about 6.8. However, it was also unexpectedly discovered that when using EC alone, exceptionally thin release coatings might be required when the cores become more perfectly spherical to provide an earlier onset of release, and/or sufficiently fast releasing pellets at pH 6.8. Exceptionally thin release coatings are difficult to manufacture consistently, and even when well-made, are more prone to leakage, which can result in premature release of API in the stomach, and/or spikes of release in the intestinal tract causing GI distress, poor uptake, or varying exposure.

As an alternative to thinner release coatings, it was unexpectedly discovered that HPMC and mixtures of HPMC and ethyl cellulose can be applied with sufficient thickness to avoid leakage, while at the same time providing rapid onset of release and faster releasing coatings at the appropriate time at pH 6.8. It is also understood that greater flexibility in coating thickness may offer a technical manufacturing advantage by improving quality assurance and control.

It has been unexpectedly discovered that faster releasing formulations provide both a higher and better sustained exposure to the host animal being treated. For example, it has also been discovered that if the release is too slow, the kidney clearance rate may compete with the absorption rate, leading to lower sustained circulating levels of API and a lower therapeutic benefit. Accordingly, it is to be understood that the sustained release is advantageously faster than the kidney clearance rate. In addition, if release is too slow, then intact pellets are observed in the feces, leading to lower sustained circulating levels of API and a lower therapeutic benefit.

It has been discovered herein that a faster pH 6.8 assay release profile surprisingly correlates to a sustained, and minimally varying circulating level of API in vivo over at least 2 hours, at least 3 hours, at least 4 hours, at least 5 hours, at least 6 hours, or at least 8 hours.

Figure 3:
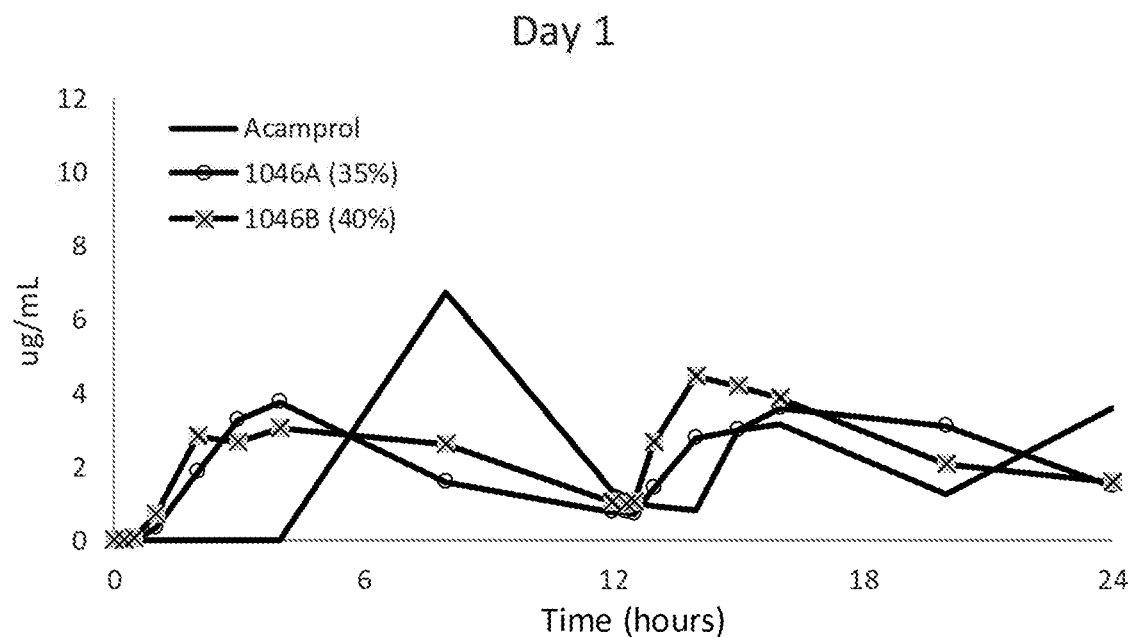
FIG. 3 shows the observed concentration of circulating acamprosate in dogs for formulations described herein compared against a Reference tablet for dosing Day 1. Dosing for each formulation was normalized to 2×333 mg acamprosate calcium, BID for each example.

For example, pellets are described herein where a dose corresponding to 666 mg of acamprosate calcium provides 1-5 µg/mL circulating in a host animal for nearly 12 hours, and 2-5 µg/mL circulating in a host animal for more than 6 hours, as shown in FIG. 3.

In addition, it has been observed herein that release coatings comprising, consisting essentially of, or consisting of HPMC or a mixture of HPMC and ethyl cellulose may provide better API recovery. It has been observed herein that coatings comprising, consisting essentially of, or consisting of HPMC or a mixture of HPMC and ethyl cellulose may provide greater than about 80%, greater than about 85% greater than about 90%, greater than about 92%, or even greater than about 95% API recovery compared to ethyl cellulose coatings, which often provide 60% API recovery.

In another embodiment, pellets are described herein that exhibit lower leak-through compared to conventional pellets, such as pellets with ethyl cellulose coatings. Leak-through can cause GI distress, and therefore, thicker enteric coatings may be necessary. It has been discovered herein that the release coatings described herein allow for thinner enteric coatings to be used. The consequence of thinner enteric coatings is that premature release at pH 1.2 is still mitigated, and faster and more complete dissolution of the enteric coating at pH 6.8 is achieved. Thus, the delay in starting release at pH 6.8 is minimized, as shown in FIG. 3 where the pellets described herein reach a sustained dose of >1 µg/mL in about 1 hour, whereas Acamprol does not begin circulating until after 4 hours.

In addition, it has been unexpectedly discovered herein that release coatings comprising, consisting essentially of, or consisting of HPMC or a mixture of HPMC and ethyl cellulose are sufficiently resilient to allow the use of aqueous dispersions of enteric coatings to be used in the coating process. Many conventional enteric coating compositions include organic solvents, such as acetone and/or isopropanol. It was observed that organic solvents were difficult to remove using state of the art techniques. For example, residual isopropanol was routinely found at levels exceeding 3000 ppm, 4000 ppm, and even 5000 ppm, even after drying for several hours, extended curing times, using enteric coating compositions that included a higher acetone/isopropanol ratio, using alternative excipients, changing spraying equipment, and lowering enteric coating levels and thicknesses. In all cases, isopropanol levels were still above optimal levels.

It was surprisingly discovered that even with the highly soluble acamprosate calcium API, and a release coating designed to provide rapid onset and rapid release of API at neutral pHs, the release coatings described herein allowed for the use of aqueous enteric coating compositions. Accordingly, also described herein are pellets that meet low threshold levels of residual organic solvent, and also pellets that are substantially free of, or completely free of residual organic solvents, such as acetone and isopropanol.

In an alternative embodiment, the pellets described herein include an enteric coating comprising a release-modifying agent comprising one or more polymers of methacrylic acid, such as a Eudragit polymer, and ethyl cellulose and/or HPMC. Without being bound by theory, it is believed herein that release coatings comprising, consisting essentially of, or consisting of a mixture of a polymer of methacrylic acid, such as a Eudragit polymer, and ethyl cellulose and/or HPMC may provide better PK performance characteristics compared to ethyl cellulose coatings. For example, release coatings comprising, consisting essentially of, or consisting of a mixture of a polymer of methacrylic acid, such as a Eudragit polymer, and ethyl cellulose and/or HPMC may provide near-zero, or zero release at pH 1.2, but fast and more complete release at pH 6.8.

Other alternative enteric coatings are also described herein, including coatings described in EP 0 453 001 A1, other methacrylic acid copolymers, methylhydroxypropylcellulose phthalate, poly(methacrylic acid, methyl methacrylates), and the like, and any combination of the foregoing. Poly(methacrylic acid, methyl methacrylate) 1:1 (Eudragit® L 100; methacrylic acid copolymer, USP/NF type A) and poly(methacrylic acid, methyl methacrylate) 1:2 (Eudragit® S; methacrylic acid copolymer, USP/NF type B) are described herein.

The pellet formulations described herein can optionally contain one or more additional additives such as lubricants, colorants, flow agents, glidants, fillers, perfumes, flavor masking agents, flavors, flavor enhancers, such as sweeteners, (both artificial and natural), effervescent agents, and the like, and any combination of the foregoing.

Illustrative lubricants include adipic acid, magnesium stearate, calcium stearate, zinc stearate, hydrogenated vegetable oils, sodium chloride, sterotex, polyoxyethylene, glyceryl monostearate, talc, polyethylene glycol, sodium benzoate, sodium lauryl sulfate, magnesium lauryl sulfate, sodium stearyl fumarate, light mineral oil and the like, waxy fatty acid esters, such as glyceryl behenate, sold as "Compritol" products, commercial lubricants include "Stear-O-Wet" and "Myvatex TL", and the like, and any combination of the foregoing.

Illustrative glidants include starch, talc, lactose, stearates, dibasic calcium phosphate, magnesium carbonate, magnesium oxide, calcium silicate, Cabosil, Syloid, and silicon dioxide aerogels, and the like, and any combination of the foregoing.

Illustrative fillers to increase the bulk of the sachet include calcium sulfate, both di- and tri-basic, starch, calcium carbonate, microcrystalline cellulose, modified starches, lactose, sucrose, mannitol, sorbitol, and the like, and any combination of the foregoing.

Illustrative flavors include natural and synthetic flavoring liquids, volatile oils, synthetic flavor oils, flavoring aromatics, oils, liquids, oleoresins and extracts derived from plants, leaves, flowers, fruits, stems and combinations thereof, such as citric oils, such a lemon, orange, grape, lime and grapefruit and fruit essences, including apple, pear, peach, grape, strawberry, raspberry, cherry, plum, pineapple, apricot, or other fruit flavors. Other Illustrative flavorings include aldehydes and esters, such as benzaldehyde (cherry, almond); citral, i.e., alpha-citral (lemon, lime); neral, i.e., beta-citral (lemon, lime); decanal (orange, lemon); aldehyde C-8 (citrus fruits); aldehyde C-9 (citrus fruits); aldehyde C-12 (citrus fruits); tolyl aldehyde (cherry, almond); 2,6-dimethyloctanal (green fruit); 2-dodedenal (citrus, mandarin); and the like, and any combination of the foregoing.

Illustrative sweeteners include glucose (corn syrup), dextrose, invert sugar, fructose, and mixtures thereof (when not used as a carrier); saccharin and its various salts, such as the sodium salt; dipeptide sweeteners such as aspartame; dihydro-chalcone compounds, glycyrrhizin; *Stevia Rebaudiana* (Stevioside); chloro derivatives or sucrose such as sucralose; and sugar alcohols such as sorbitol, mannitol, xylitol, and the like, hydrogenated starch hydrolysates and the synthetic sweeteners such as 3,6-dihydro-6-methyl-1-1-1,2,3-oxathiazin-4-one-2,2-dioxide, particularly the potassium salt (acesulfame-K), and sodium and calcium salts thereof.

Effervescent agents may be included to aid in masking the objectionable taste of active ingredients.

Illustrative color additives include food, drug and cosmetic colors (FD&C), drug and cosmetic colors (D&C) or external drug and cosmetic colors (Ext. D&C). These colors are dyes, lakes, and certain natural and derived colorants. Useful lakes include dyes absorbed on aluminum hydroxide or other suitable carriers.

An appropriate dosage of an active ingredient or pharmaceutical composition comprising an active ingredient may be determined according to any one of several well-established protocols. For example, animal studies such as studies using mice, rats, dogs, and/or monkeys may be used to determine an appropriate dose of a pharmaceutical compound. Results from animal studies may be extrapolated to determine doses for use in other species, such as for example, humans. Is has been determined herein that dogs are a useful species for correlating the in vitro release assays at pH 1.2 and pH 6.8 with desired PK profiles. Pellets that release API rapidly, such as at least 70% in 30 minutes and at least 90% in 90 minutes provide high circulating levels of API (1-5 µg/mL) in circulation for extended periods of time (12 hours).

The pellets, and formulations thereof, described herein are useful for treating a wide range of diseases, including but not limited to neurotransmission or cognitive disorders that are characterized as a glutamate-GABA imbalance, disorders characterized with disrupted or dysregulated ERK signaling pathway or rasopathies resulting in abnormalities in brain development, learning, memory and cognition. Illustrative diseases include, but are not limited to, Autism Spectrum Disorders, Pervasive Development Disorders—Not Otherwise Specified, Idiopathic Autism, Fragile X Syndrome, Asperger's Syndrome, Rhett's Syndrome, Childhood Disintegrative Disorder as further referenced in Diagnostic and Statistical Manual of Mental Disorders V, Alcohol dependence, tinnitus, sleep apnea, Parkinson's Disease, levodopa-induced dyskinesias in Parkinson's Disease (PD), Alzheimer's Disease (AD), Huntington's Disease (HD), Cortical spreading depression, migraine, schizophrenia, anxiety, tardive dyskinesia, spasticity, multiple sclerosis, various types of pain, or binge eating, subjects having or at risk for age-related cognitive impairment, Mild Cognitive Impairment (MCI), dementia, prodromal AD, post-traumatic stress disorder (PTSD), bipolar disorder, amyotrophic lateral sclerosis (ALS), cancer-therapy-related cognitive impairment, drug induced or toxin induced cognitive impairments, compulsive behavior, substance addiction, Down's syndrome, a neurological disorder and/or mental retardation in order to diminish, halt, ameliorate or prevent one or more of the neurological deficiencies or symptoms associated with the disorder (e.g., benign childhood epilepsy, temporal lobe epilepsy, visual spatial defects, anxiety, aggression, hyperactivity, agitation, repetitive behaviors, abnormal or limited social interactions, language and learning difficulties, and/or combinations thereof).

In certain embodiments, children with mental retardation, Autism Spectrum Disorders, Down's Syndrome and Fragile X Syndrome can be treated with a formulation described herein. The children can be treated during infancy (between about 0 to about 1 year of life), childhood (the period of life between infancy and puberty) and during puberty (between about 8 years of life to about 18 years of life).

The amount of an active ingredient that will be effective in the treatment of a disease in a subject will depend, in part, on the nature of the condition and can be determined by standard clinical techniques known in the art. In addition, in vitro or in vivo assays may be employed to help identify optimal dosage ranges. A therapeutically effective amount of an active ingredient to be administered may also depend on, among other factors, the subject being treated, the weight of the subject, the severity of the disease, the manner of administration, and the judgment of the prescribing physician.

The unit dose of the drug is generally about 100 mg to about 2500 mg. Preferably, the unit dose is about 200 to about 500 mg (e.g., about 333 mg). The unit dose form is typically administered 1-4 times per day, preferably 2-3 times per day.

The pellet formulations described herein are typically intended for oral administration. For example, the pellets can be packaged in sachets or straws, which are opened at the time of use, and the drug product sprinkled onto food for ingestion. Preferred foods have a pH of less than about 5.5, such as applesauce and yogurt. The pellets can also be encased in a capsule, which can either be taken as such, or the capsule can be opened and the contents sprinkled onto food for ingestion.

It is to be understood that the pellets and formulations described herein may be co-administered or adapted for coadministration with other therapeutically active compounds, such as, but not limited to, Group I mGluR antagonists, antipsychotic agents, including atypical antipsychotic compounds, neuroleptic medications, selective serotonin reuptake inhibitors (SSRIs), serotonin-norepinephrine reuptake inhibitors (SNRIs), antidepressants, anti-anxiety medications, $GABA_B$ receptor agonist, a muscarinic receptor antagonist, a stimulant, a nicotinic receptor agonist, an endocannabinoid receptor antagonist, an AMPA agonist, an a2-adrenergic agonist, or an anticonvulsant and the like.

Each publication cited herein is incorporated herein in its entirety by reference.

Examples

Acamprosate calcium drug substance is commercially available from IndSwift as a white or off-white powder, with assay % as high as 99.5%-100%. Unless otherwise indicated all excipients described herein to be used as diluents, components of the release coating, or components of the enteric coating are obtained from commercially available sources.

The API is reported to cause GI irritation, and therefore, the two current marketed formulations of acamprosate calcium are enteric-coated tablets, Campral (marketed in the United States by Forest Laboratories, and outside the US by Merck KGaA) and Acampral (Sun Pharmaceuticals). It is believed herein that pellets coated with an enteric polymer will minimize or avoid the premature release of API into the stomach when administered orally.

Illustrative target product features of the acamprosate sprinkles dosage form are summarized in the following Table.

Acamprosate sprinkles target drug product attributes

| Dosage form | Sprinkles |
|---|---|
| Strength | 333 mg per dosage unit |
| Packaging configuration | Packaged in aluminum sachets or straws |
| Stability | Stable at: |
| | 25° C./60% RH up to 6 months |
| | 40° C./75% RH up to 6 months |

Illustrative cores pellets with two different sizes/diameters were prepared. Release characteristics of the two cores sizes, and the corresponding pellets prepared therefrom were not significantly different.

The pellets described herein can be manufactured and evaluated using conventional equipment and techniques. For example, illustrative equipment is described in co-pending PCT international application No. PCT/US2016/030725.

The analytical methods used for evaluation of sprinkles, such as assay and dissolution methods are summarized in the following Tables.

Illustrative Assay Method Details for Acamprosate Calcium Sprinkles

| Parameter | | |
|---|---|---|
| Assay | Buffer | TEA (0.5%) pH adjusted to 4.0 |
| | Mobile phase | Buffer |
| | Diluent | Milli Q Water |
| | Chromatographic System | LC |
| | Detector | 210 nm |
| | Column | Cosmosil 5C18-PAQ (4.6*250 mm, 5µ) (C18) |
| | Flow rate | 0.7 mL/min |
| | Retention Time | 20 min |
| | Column Temp | 25° C. |

Illustrative Related Substances Method Details for Acamprosate Calcium Sprinkles

| Parameter | | |
|---|---|---|
| Impurity A | Buffer | $KH_2PO_4$ adjusted the pH to 6.5 |
| | Diluent | Borate buffer solution pH 10.4 |
| | Mobile phase | Buffer:Acetonitrile:Methanol (80:10:10) |
| | Sample preparation | Fluorescamine derivatization |
| | Chromatographic System | LC |
| | Detector | 261 nm |
| | Column | Discovery HS C18, 15 cm*4.6 mm, 3 µm |
| | Flow rate | 1 ml/min |
| | Retention Time | 60 min |
| Other Impurities | Buffer | TEA (0.5%) pH adjusted to 4.0 |
| | Mobile phase | Buffer |
| | Diluent | Milli Q water |
| | Chromatographic System | LC |
| | Detector | 210 nm |
| | Column | Cosmosil 5C18-PAQ (4.6*250 mm, 5 µm) |
| | Flow rate | 0.7 ml/min |
| | Retention Time | 60 min |
| | Column temperature | 25° C. |
| | Total impurities | Method A + Method B impurities |

Illustrative Dissolution Methods

| Dissolution medium | pH 1.2 for 2 hours followed by pH 6.8 for 3 hours |
|---|---|
| Apparatus | USP-II (Paddle) |
| Temperature | 37° C. ± 0.5° C. |

Example

Manufacture of Acamprosate calcium cores (#16/20 ASTM and #25/30 ASTM). Pellets with two illustrative different core sizes (#16/20 and #25/30) are described. The cores were manufactured by extrusion of wet mass of API+diluent, such as Avicel PH 101 through a mesh size of 1.2 mm or 0.8 mm. In each case, the extruded material was charged into a spheronizer at plate RPM of 2.1 for 10 min to obtain generally spherically shaped uncoated cores.

Illustrative Compositions of Acamprosate Calcium Uncoated Sprinkles (B. No. SF14000746)

|   | Component | Category | g/batch |
|---|---|---|---|
| 1 | Acamprosate calcium* | API | 500 |
| 2 | Avicel PH 101 | Diluent | 500 |
|   | Total |   | 1000 g |

|   | Component | Category | g/batch |
|---|---|---|---|
| 1 | Acamprosate calcium* | API | 600 |
| 2 | Avicel PH 101 | Diluent | 400 |
|   | Total |   | 1000 g |

Each 200 mg of sprinkles were equivalent to 100 mg or 120 mg of Acamprosate Calcium API, respectively. Assay of sprinkles was 98% w/w or greater.

Example. Dissolution of Cores

Dissolution of Acamprosate Calcium 50:50 cores in pH 6.8 buffer (#16/20 ASTM)

|   | 30 min | 60 min | 90 min | 120 min | 180 min | Infinity |
|---|---|---|---|---|---|---|
| AVG (n = 3) | 98 | 98 | 99 | 99 | 99 | 99 |
| STDEV | 1.7 | 1.0 | 1.0 | 1.2 | 1.2 | 1.0 |
| RSD | 1.73 | 1.02 | 1.01 | 1.21 | 1.21 | 1.01 |

Example. Release Coating Compositions

Illustrative Compositions for Release Coatings

| Ingredients | % w/w weight gain | Quantity in g for 200 g batch size* |
|---|---|---|
| SF16001493 (5% (+w)/w (4:1 w/w EC/HPMC coating) | | |
| Ethyl Cellulose 20 standard premium | — | 7.68 g |
| HPMC 3 cps | — | 1.92 g |
| Triethyl citrate | 25% | 2.4 g |
| IPA:Purified water | 9:1 | QS |
| SF16001518 & SF16001578 (5% (+w)/w (4:1 w/w EC/HPMC coating) | | |
| Ethyl Cellulose 10 standard premium | — | 7.68 g |
| HPMC 3 cps | — | 1.92 g |
| Triethyl citrate | 25% | 2.4 g |
| IPA:Purified water | 9:1 | QS |

Release coating compositions include a 20% excess of solids to account for potential losses in processing equipment.

Example

Intermediate release coated cores are shown in the following Table. Cores with any ratio of API:diluent, such as about 50:50 to about 80:20, including about 60:40, are useable.

| Ingredients | % W/W | SF17000105 |
|---|---|---|
| Acamprosate calcium core pellets #20/30 | — | 6.00 Kg |
| Release coating components | | Weight of pellets taken 6.0 Kg |
| Ethyl cellulose 10 cps | — | 0.1872 Kg |
| HPMC 3 cps | — | 0.1248 Kg |
| Triethyl Citrate | 25% | 0.078 Kg |
| IPA:water | 9:1 | 4.484 g (4.036 Kg IPA + 0.4485 Kg $H_2O$) |

Release coating compositions include a 20% excess of solids to account for potential losses in processing equipment.

Illustrative Manufacturing Procedure for Release Coating

| Solution preparation | Machine Controls (GPCG 1.1 bottom spray) |
|---|---|
| Solution prepared for 5% w/w weight gain | Nozzle diameter - 0.8 mm |
| Overages considered for 20% w/w weight gain | Bottom Plate - Type C |
| Ethyl Cellulose & HPMC 3 cps added into IPA:water solution with stirring | Inlet Temperature - 35° C.-50° C. |
| Triethyl citrate added into Ethyl Cellulose solution | Product Temperature - 30° C.-40° C. |
| Solution is passed through ASTM 60# mesh before using it for coating | Exhaust Temperature - 40° C.-50° C. |

Example

Enteric coated pellets. Release coated cores are further coated with an enteric coating, such as Eudragit L 100 55 polymer. The formula composition for the enteric coating is shown in the following Table.

Illustrative Formula Compositions for Enteric Coating

| Ingredients | % w/w weight gain | Quantity in grams for 200 g batch size[a] |
|---|---|---|
| For 30%, 35% and 40% (+w)/w enteric coating (SF16001141 & SF16001460)[c] | | |
| Eudragit L 100 55 (polymer solids) | — | 54.86 |
| Triethyl citrate | 25 | 13.71 |
| Talc | 50 | 27.43 |
| Acetone:IPA:Purified water (Diluent) | 38.1:57.13:4.77 | QS |
| For 40% & 50% (+w)/w enteric coating (SF16001518 & SF16001578) | | |
| Eudragit L 100 55 (polymer solids) | — | 68.57 |
| Triethyl citrate | 25 | 17.15 |
| Talc | 50 | 34.27 |
| Acetone:IPA:Purified water (Diluent) | 38.1:57.13:4.77 | QS |

[a] coating solution is prepared for 40% (+w)/w weight gain over release coated cores, however coating is performed to provide each of 30%, 35% and 40% (+w)/w.
[b] samples are collected after 30% (+w)/w and batch continued to obtain 35% and 40% (+w)/w sample.
[c] samples are collected after 40% (+w)/w and batch continued to obtain 50% (+w)/w sample.

Example

An illustrative manufacturing procedure for the enteric coating is shown in the following Table.

Illustrative Manufacturing Procedure for Enteric Coating

| Solution preparation | Machine Controls (GPCG 1.1 bottom spray) |
|---|---|
| Solution prepared for 50% (+w)/w weight gain | Nozzle diameter - 1.2 mm |
| Overages considered for 20% w/w weight gain | Bottom Plate - Type C |
| Eudragit L 100 55 was added into 50% of the diluent under stirring | Inlet Temperature - 25° C.-35° C. |
| Talc and Triethyl citrate were added into 50% of the diluent under Homogenizer | Product Temperature - 25° C.-30° C. |
| Homogenized suspension was added into Eudragit L 100 55 under stirring | Exhaust Temperature - 30° C.-40° C. |
| Solution is passed through ASTM 60# mesh before use for coating | |

The sprinkles are intended to be administered in an edible matrix, such as applesauce or yogurt. It is understood herein that most brands of applesauce have a pH in the range of 3-3.6. To determine the drug release in pH 3.0 and 4.5, a dissolution study was conducted on the sprinkles, and the results are shown in following Tables.

Dissolution of 50% Enteric-Coated Sprinkles in pH 3.0 Buffer

|  | 30 min | 60 min | 120 min | 180 min |
|---|---|---|---|---|
| Sample 1 | 0 | 0 | 0 | 1 |
| Sample 2 | 0 | 0 | 0 | 2 |
| Sample 3 | 0 | 0 | 0 | 1 |
| Avg | 0 | 0 | 0 | 1 |
| Stdev | 0.0 | 0.0 | 0.0 | 0.6 |
| RSD | 0 | 0 | 0 | 60.00 |

Dissolution of 50% Enteric-Coated Sprinkles in pH 4.5 Buffer

|  | 30 min | 60 min | 120 min | 180 min |
|---|---|---|---|---|
| Sample 1 | 0 | 0 | 1 | 2 |
| Sample 2 | 0 | 0 | 1 | 3 |
| Sample 3 | 0 | 0 | 1 | 2 |
| Avg | 0 | 0 | 1 | 2 |
| Stdev | 0 | 0 | 0 | 0.6 |
| RSD | 0 | 0 | 0 | 30.00 |

Drug release of sprinkles in pH 3.0 and 4.5 was observed to be NMT 2% after 120 min.

Example

Stability of Acamprosate calcium pellets. Pellet samples are loaded on stability, as follows:
 Packaging—Sprinkles are weighed into aluminum sachets and sealed.
 Fill weight—800-900 mg (Sprinkles weighed are equivalent to 333 mg Acamprosate calcium)
 Conditions—25° C./60% RH or 40° C./75% RH
 Time points—Initial, 1, 3, 6 & 12 months
 Evaluation—Assay, related substances and dissolution Example. Illustrative Acamprosate Calcium Sprinkles and Dissolution Profiles Dissolution of Acamprosate Calcium Sprinkles

| Example | SF16001518 | SF16001518 | SF16001880 | SF16001880 |
|---|---|---|---|---|
| Release Coating | 5% (+w)/w (1:4 w/w HPMC 3 cps/EC 10 cps) | 5% (+w)/w (1:4 w/w HPMC 3 cps/EC 10 cps) | 5% (+w)/w (2.5:2.5 w/w HPMC 3 cps/EC 10 cps) | 5% (+w)/w (2.5:2.5 w/w HPMC 3 cps/EC 10 cps) |
| Enteric Coating | 40% (+w)/w Eudragit coating | 50% (+w)/w Eudragit coating | 40% (+w)/w Eudragit coating | 50% (+w)/w Eudragit coating |
|  |  | pH 1.2 |  |  |
| 2 hr | 8 | 5 | 10 | 5 |
|  |  | pH 6.8 |  |  |
| 30 min | 76 | 72 | 96.0 | 91 |
| 60 min | 86 | 84 | 96.0 | 91 |
| 90 min | 90 | 88 | 96.0 | 92 |
| 120 min | 92 | 90 | 97.0 | 92 |
| 180 min | 95 | 93 | 96.0 | 91 |

Dissolution of Acamprosate Calcium Sprinkles

| Example | SF16001857 | SF16001857 | SF17000105 |  |
|---|---|---|---|---|
| Release Coating | 5% (+w)/w (5:0 w/w HPMC 3 cps/EC 10 cps) | 5% (+w)/w (5:0 w/w HPMC 3 cps/EC 10 cps) | 5% (+w)/w (2:3 w/w HPMC 3 cps/EC 10 cps) |  |
| Enteric Coating | 40% (+w)/w Eudragit coating | 50% (+w)/w Eudragit coating | 40% (+w)/w Eudragit coating |  |
|  | pH 1.2 |  | pH 1.2 | % RSD |
| 2 hr | 8 | 4 | 2 | 0 |
|  | pH 6.8 |  | pH 6.8 | % RSD |
| 30 min | 97 | 95 | 68 | 0.84 |
| 60 min | 98 | 96 | 89 | 0.64 |
| 90 min | 99 | 96 | 94 | 0.61 |

-continued

| Example | SF16001857 | SF16001857 | SF17000105 | |
|---|---|---|---|---|
| 120 min | 99 | 97 | 96 | 0.61 |
| 180 min | 99 | 96 | 98 | 0.60 |

Dissolution of Acamprosate Calcium Sprinkles

| SF16002144 (5% (+w)/w HPMC 3 cps based coating) | | | | | |
|---|---|---|---|---|---|
| 40% (+w)/w Eudragit Coating | | 45% (+w)/w Eudragit Coating | | 50% (+w)/w Eudragit Coating | |
| pH 1.2 | % RSD | pH 1.2 | % RSD | pH 1.2 | % RSD |
| 2 hr | 1 | 0.0 | 1 | 0.0 | 0 | 0.0 |

| | pH 6.8 | % RSD | pH 6.8 | % RSD | pH 6.8 | % RSD |
|---|---|---|---|---|---|---|
| 30 min | 104 | 0.50 | 98 | 0.55 | 99 | 1.72 |
| 60 min | 105 | 0.72 | 99 | 1.79 | 100 | 1.38 |
| 90 min | 106 | 0.53 | 100 | 1.74 | 100 | 1.12 |
| 120 min | 106 | 0.72 | 101 | 2.19 | 100 | 1.50 |
| 180 min | 106 | 0.73 | 101 | 1.77 | 101 | 1.13 |

Dissolution of Acamprosate Calcium Sprinkles

| Example | | | |
|---|---|---|---|
| SF16002241 | SF16002302 | SF1700009 (Comparative example) | |
| Release coating | | | |
| 5% (+w)/w (4:1 w/w HPMC 3 cps/EC 10 cps) | 5% (+w)/w (3:2 w/w HPMC 3 cps/EC 10 cps) | 5% (+w)/w EC based coating | |
| Enteric coating | | | |
| 40% (+w)/w Eudragit Coating | 40% (+w)/w Eudragit Coating | 40% (+w)/w Eudragit Coating | |
| pH 1.2 | % RSD | pH 1.2 | % RSD | pH 1.2 | % RSD |
| 2 hr | 1 | 0.0 | 7 | 17.32 | 6 | 8.70 |

| | pH 6.8 | % RSD | pH 6.8 | % RSD | pH 6.8 | % RSD |
|---|---|---|---|---|---|---|
| 30 min | 97 | 3.2 | 99 | 0.59 | 40 | 1.24 |
| 60 min | 98 | 2.9 | 100 | 0.58 | 57 | 1.41 |
| 90 min | 99 | 3.5 | 100 | 0.99 | 68 | 1.21 |
| 120 min | 99 | 3.0 | 100 | 0.99 | 74 | 1.12 |
| 180 min | 99 | 2.8 | 99 | 0.59 | 80 | 0.64 |

Dissolution of Acamprosate Calcium Pellets

| Example | | | | |
|---|---|---|---|---|
| SF17000459 | SF17000595 | SF17001046A | SF17001046B | |
| Release coating | | | | |
| 5% (+w)/w (2:3 w/w HPMC 3 cps/EC 10 cps) | 5% (+w)/w (2:3 w/w HPMC 3 cps/EC 10 cps) | 5% (+w)/w (4:1 w/w HPMC 3 cps/EC 10 cps) | 5% (+w)/w (4:1 w/w HPMC 3 cps/EC 10 cps) | |
| Enteric coating | | | | |
| 40% (+w)/w aqueous Eudragit (small scale) | 40% (+w)/w aqueous Eudragit (large scale) | 35% (+w)/w aqueous Eudragit (large scale) | 40% (+w)/w aqueous Eudragit (large scale) | |
| pH 1.2 | % RSD | pH 1.2 | % RSD | pH 1.2 | % RSD | pH 1.2 | % RSD |
| 2 hr | 4 | 0.00 | 0 | 0.00 | 0 | 0.0 | 0 | 0.0 |

| | pH 6.8 | % RSD | pH 6.8 | % RSD | pH 6.8 | % RSD | pH 6.8 | % RSD |
|---|---|---|---|---|---|---|---|---|
| 30 min | 80 | 1.45 | 73 | 1.23 | 95 | 1.5 | 92 | 1.1 |
| 60 min | 93 | 0.63 | 91 | 0.70 | 94 | 1.5 | 92 | 0.9 |
| 90 min | 97 | 0.61 | 95 | 0.56 | 95 | 1.1 | 92 | 1.2 |
| 120 min | 99 | 0.61 | 96 | 0.58 | 95 | 0.9 | 92 | 1.3 |
| 180 min | 99 | 0.03 | 97 | 0.58 | 95 | 1.0 | 93 | 0.9 |

Dissolution of Acamprosate Calcium Pellets

| Example | SF17001046B | | SF17001511 | |
|---|---|---|---|---|
| Release coating | 5% (+w)/w (4:1 w/w HPMC 3 cps/EC 10 cps) | | 5% (+w)/w (4:1 w/w HPMC 3 cps/EC 10 cps) | |
| Enteric coating | 40% (+w)/w Eudragit (small scale) | | 40% coating (large scale) | |
| | pH 1.2 | % RSD | pH 1.2 | % RSD |
| 2 hr | 0.0 | 0.0 | 2 | 31.0 |
| | pH 6.8 | % RSD | pH 6.8 | % RSD |
| 30 min | 92 | 1.1 | 97 | 3.2 |
| 60 min | 92 | 0.9 | 98 | 3.2 |
| 90 min | 92 | 1.2 | 98 | 3.3 |
| 120 min | 92 | 1.3 | 98 | 2.9 |
| 180 min | 93 | 0.9 | 98 | 3.1 |

Example

Stability studies of Acamprosate Calcium sprinkles on storage. Dissolution of sprinkles subjected to open petri plate.

Example SF17000595 (40% (+w)/w Enteric Coating)

|  | Initial | | 2 weeks open exposure at 40° C./75% RH | | 2 weeks at −20° C. in sachet | | 2 weeks at 2-8° C. in sachet | |
|---|---|---|---|---|---|---|---|---|
|  | % Release | % RSD | % Release | % RSD | % Release | % RSD | % Release | % RSD |
| 2 Hr Acid Stage | 0 | 0 | 0 | 0 | 0 | 0 | 0 | 0 |
| 30 Min | 73 | 1.23 | 75 | 1.89 | 76 | 2.81 | 75 | 0.95 |
| 60 Min | 91 | 0.70 | 90 | 1.59 | 91 | 0.80 | 90 | 0.78 |
| 90 Min | 95 | 0.56 | 94 | 0.72 | 95 | 1.52 | 94 | 0.75 |
| 120 Min | 96 | 0.58 | 96 | 0.02 | 96 | 0.78 | 96 | 1.49 |
| 180 Min | 97 | 0.58 | 96 | 0.76 | 97 | 0.78 | 96 | 0.76 |

Dissolution of Sprinkles Subjected to Open Petri Plate

|  | SF16001857 (50% (+w)/w enteric coating) | | | SF16001880 (50% (+w)/w enteric coating) | | |
|---|---|---|---|---|---|---|
|  | Initial | 2 weeks 40° C./75% RH | 4 weeks 40° C./75% RH | Initial | 2 weeks 40° C./75% RH | 4 weeks 40° C./75% RH |
| 2 Hr Acid Stage | 4 | 2 | 2 | 5 | 3 | 3 |
| 30 Min | 95 | 95 | 96 | 91 | 95 | 96 |
| 60 Min | 96 | 96 | 97 | 91 | 97 | 96 |
| 90 Min | 96 | 97 | 97 | 92 | 98 | 97 |
| 120 Min | 97 | 98 | 98 | 92 | 97 | 97 |
| 180 Min | 96 | 99 | 99 | 91 | 98 | 98 |

Dissolution of Sprinkles Subjected to Open Petri Plate

|  | SF17001046A (35% (+w)/w Eudragit coating) | | | SF17001046B (40% (+w)/w Eudragit coating) | | |
|---|---|---|---|---|---|---|
|  | Initial | 2 weeks open exposure (40° C./75% RH) | 4 weeks open exposure (40° C./75% RH) | Initial | 2 weeks open exposure 40° C./75% RH | 4 weeks open exposure (40° C./75% RH) |
| 2 Hr Acid Stage | 0 | 1 | 0 | 0 | 0 | 0 |
| 30 Min | 95 | 96 | 96 | 92 | 91 | 95 |
| 60 Min | 94 | 96 | 96 | 92 | 92 | 95 |
| 90 Min | 95 | 96 | 96 | 92 | 91 | 95 |
| 120 Min | 95 | 96 | 96 | 92 | 92 | 96 |
| 180 Min | 95 | 97 | 96 | 93 | 92 | 96 |
| Water content (% w/w) | 2.5 | 2.3 | 2.5 | 2.2 | 2.1 | 2.8 |
| Assay (% w/w) | 97.3 | 95.8 | 95.2 | 94.0 | 94.0 | 92.1 |

Dissolution of Sprinkles (600 mg Sachets) on Storage at 40° C./75% RH

|  | SF17001046A (35% (+w)/w Eudragit coating) | | | SF17001046B (40% (+w)/w Eudragit coating) | | |
|---|---|---|---|---|---|---|
|  | Time Interval | | | | | |
|  | Initial | 1 Month | 2 months | Initial | 1 months | 2 months |
|  | Assay (%) | | | | | |
|  | 97.3 | 94.9 | 96.0 | 94.0 | 94.5 | 93.0 |
|  | Water content (% w/w) | | | | | |
|  | 2.5 | 2.2 | 2.0 | 2.2 | 1.9 | 2.0 |
|  | Total impurities (%) | | | | | |
|  | 0.024 | 0.024 | 0.024 | 0.023 | 0.023 | 0.023 |
|  | Dissolution (average, N = 3) | | | | | |
| 120 min (pH 1.2 buffer) | 0 | 0 | 0 | 0 | 0 | 0 |
|  | Dissolution in pH 6.8 buffer | | | | | |
| 30 min | 94 | 97 | 98 | 92 | 97 | 95 |
| 60 min | 94 | 98 | 99 | 92 | 96 | 96 |
| 90 min | 95 | 98 | 98 | 92 | 96 | 96 |
| 120 min | 95 | 98 | 97 | 92 | 96 | 95 |
| 180 min | 95 | 98 | 98 | 93 | 96 | 95 |

Dissolution of Sprinkles (200 mg Sachets) on Storage at 40° C./75% RH

|  | SF17001046A (35% (+w)/w Eudragit coating) | | SF17001046B (40% (+w)/w Eudragit coating) | |
| --- | --- | --- | --- | --- |
| Time Interval | 1 Month | 2 months | 1 months | 2 months |
| Assay (%) | 94.4 | 96.0 | 94.2 | 93.7 |
| Water content (% w/w) | 2.2 | 2.3 | 2.1 | 2.5 |
| Total impurities (%) | 0.023 | 0.023 | 0.019 | 0.023 |
| Dissolution (average, N = 3) | | | | |
| 120 min (pH 1.2 buffer) | 0 | 0 | 0 | 0 |
| Dissolution in pH 6.8 buffer | | | | |
| 30 min | 97 | 98 | 96 | 97 |
| 60 min | 98 | 99 | 96 | 97 |
| 90 min | 98 | 98 | 96 | 96 |
| 120 min | 98 | 97 | 96 | 96 |
| 180 min | 98 | 98 | 96 | 97 |

Example

PK studies of Campral in dogs (Reference example). Pharmacokinetic studies are conducted in beagle dogs at Covance's Madison, Wisconsin facility. This accepted animal model is used to understand how active ingredient is absorbed, distributed and eliminated. It should be noted that beagle dogs are used as the animal model for Campral and published research is available for comparison (Kathleen Haberny-FDA Review, Adam Wasserman-FDA review and Rhee et al., 2008 a, b). The study allows the demonstration of the baseline profile for the existing 333 mg enteric-coated tablet across several dose ranges, and at the same time compare a simple "naked" formulation with no excipients where the active ingredient was dissolved in an aqueous solution.

The studies confirmed three findings: the initial peak concentration ($C_{max}$) of the active drug in the body increased substantially though deliver as a non-enteric coated solution, second the amount of "naked" drug systemically available (bioavailability) was considerably higher than the Campral tablet, and lastly, a "naked" drug substantially increased G.I. intolerability across all dosages for all dogs. The completed formulation study demonstrated the challenges of a simple, "naked" aqueous solution was impractical path for administering this drug.

Example

PK studies of Examples disclosed herein in dogs, and compared to Campral and Acamprol tablets. In a 7 day study, dogs are dosed daily at 666 mg or 1,332 mg BID for a maximum aggregate exposure of 2,664 mg per day. All dogs are male non-naïve beagle dogs from the Covance stock colony. At dosing, the animals weigh 9.4 to 12.0 kg and are young adult/adult. Animals are identified with individually numbered cage cards or an implantable microchip identification device (IMID). Animals are selected for test based on overall health and body weight. The study is conducted under fed conditions and animals are given Certified Canine Diet #5007 and food is provided ad libitum. Water is provided fresh daily ad libitum. Animals are housed in stainless steel cages in a room set to maintain a temperature of 20 to 26° C., a relative humidity of 50±20%, and a 12-hour light/12-hour dark cycle. As necessary, the 12-hour dark cycle is temporarily interrupted to accommodate study procedures. Sprinkles are filled into rapidly dissolving capsules at Covance and portioned out for twice-daily administration throughout the dosing period. Campral tablets are administered twice-daily throughout the dosing period. Any remaining tablets or filled capsules are stored at ambient temperature. Individual doses are orally administered as a fixed dose of 2 or 4 capsules/tablets per animal (666 or 1332 mg per animal) twice daily, approximately 12 hours apart, for a maximum total dose of 8 capsules/tablets per day (2664 mg per animal) followed by approximately 10 mL of water.

Twice daily (a.m. and p.m.), animals are observed for mortality and signs of pain and distress. Cage-side observations for general health and appearance are done once daily. Any unusual observations noted throughout the duration of the study are recorded in the raw data. Body weights are taken at the time of animal selection and on Day 1 of dose administration. On Days 1 and 7, blood (approximately 2 mL) are collected from a jugular vein into tubes containing $K_2EDTA$ anticoagulant pre-dose and at 0.25, 0.5, 1, 2, 4, 8, 12, 24, and 48 (Day 7 only) hours post-dose. The 12-hour blood samples are collected prior to the 12-hour dose and the 24-hour blood samples are collected prior to the Day 2 dose.

Example

PK results for Examples disclosed herein. A total of 1332 mg (effective dose) of acamprosate calcium formulation was filled into groups of capsules. For SF17001046A, each capsule contained 787 mg of the sprinkle formulation, which corresponds to 333 mg of API. For SF17001046B, each capsule contained 816 mg of the sprinkle formulation, which corresponds to 333 mg of API. All animals were fed (about 150 g) with conventional dog feed approximately 1 h prior to each dosing. Water was provided ad libitum during the study. Approximately 5 mL of Milli-Q water was administered through cheek pouch after capsule/tablet dosing.

Blood samples were collected serially at pre-dose, 0.25, 1, 2, 4, 8, 12 (prior to second dose), 13, 16, 20, 24 hours post first dose. At each time 2 mL of blood was withdrawn from jugular vein and transferred into a labeled $K_2EDTA$ coated tubes. Blood samples were centrifuged and harvested plasma was stored below −60° C. until shipment to Advinus Therapeutics Limited for bioanalysis. The plasma samples were analyzed for the quantification of Acamprosate using a fit-for purpose LC-MS/MS method with a lower limit of quantification of 0.025 μg/mL. The pharmacokinetic parameters of test formulations were calculated using validated Phoenix® WinNonlin® software (version 6.3)

Pharmacokinetic Parameters (Mean±SD)

| Test Compound | Day | $C_{max}$ (μg/mL) | $AUC_{last}$ (μg·h/mL) | $AUC_{0-12\,h}$ (μg·h/mL) | $AUC_{12-24\,h}$ (μg·h/mL) | % F |
|---|---|---|---|---|---|---|
| Campral (Reference example) | 1 | 5.06 ± 2.05 | 32.3 ± .655 | 16.1 ± 10.8 | 16.2 ± 15.7 | NA |
|  | 4 | 4.02 ± 1.97 | not determined | 26.7 ± 13.6 | not determined | NA |
| Acamprol (Reference example) | 1 | 3.54 ± 1.77 | 30.3 ± 9.56 | 10.3 ± 9.41 | 20.0 ± 8.90 | NA |
|  | 4 | 6.82 ± 2.90 | 63.0 ± 18.5 | 37.9 ± 12.5 | 25.1 ± 6.27 | NA |
| Acamprol (Reference example) | 1 | 4.81 ± 4.44 | 37 ± 31.9 | 19.8 ± 19.3 | 17.2 ± 17.9 | NA |
|  | 4 | 11.1 ± 2.71 | 93.7 ± 40.3 | 39.7 ± 30 | 54 ± 12.4 | NA |
| SF16002241 | 1 | 4.04 ± 0.621 | 49.0 ± 7.98 | 26.7 ± 4.87 | 22.4 ± 5.86 | 162 |
|  | 4 | 4.02 ± 0.633 | 55.8 ± 11.4 | 27.0 ± 5.54 | 28.8 ± 9.96 | 89 |
| SF17001046A | 1 | 4.23 ± 0.798 | 54.6 ± 7.45 | 22.9 ± 4.32 | 31.7 ± 5.81 | 148 |
|  | 4 | 7.56 ± 1.84 | 67.3 ± 10.3 | 31.4 ± 9.04 | 35.9 ± 11.7 | 72 |
| SF17001046B | 1 | 5.30 ± 1.5 | 58.9 ± 10 | 26.4 ± 6.43 | 32.5 ± 5.51 | 159 |
|  | 4 | 8.31 ± 2.9 | 92 ± 27.8 | 38.6 ± 8.29 | 53.5 ± 21.3 | 98 |

FIG. 1 shows the Day 1 and Day 4 $C_{max}$ for each test article. The data demonstrated that the exposures by Day 4 were not significantly different among all test articles.

Figure 2:
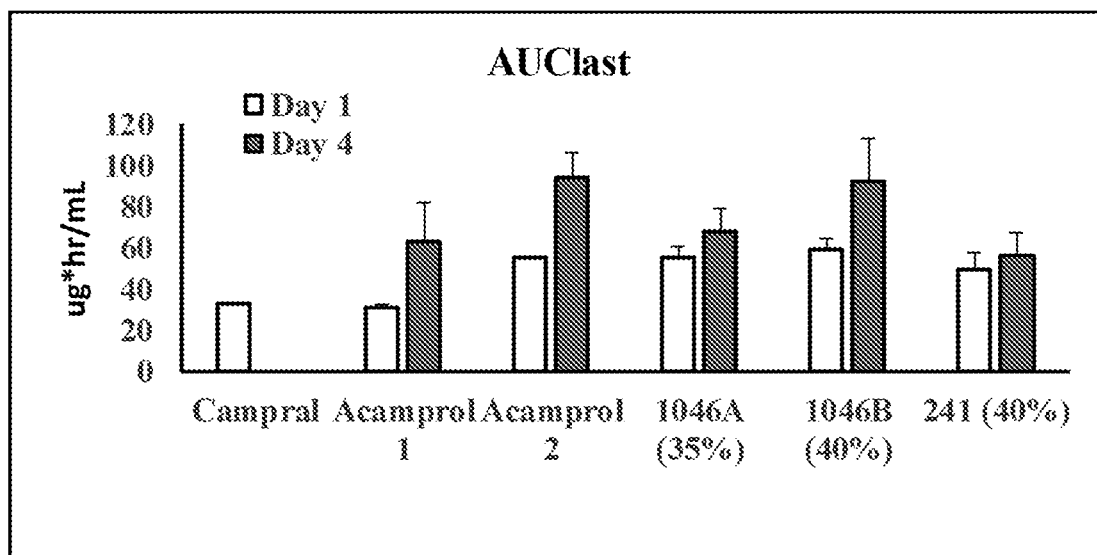
FIG. 2 shows the $AUC_{last}$ in dogs for formulations described herein compared against Reference tablets for dosing Days 1 and 4. Dosing for each formulation was normalized to 2×333 mg acamprosate calcium, BID for each example. There were not any observed statistical differences between any of the tested formulations on Day 4.

FIG. 2 shows the Day 1 and Day 4 $AUC_{last}$ for each test article. The data demonstrated that the exposures by Day 4 were not significantly different among all test articles.

Figure 4:
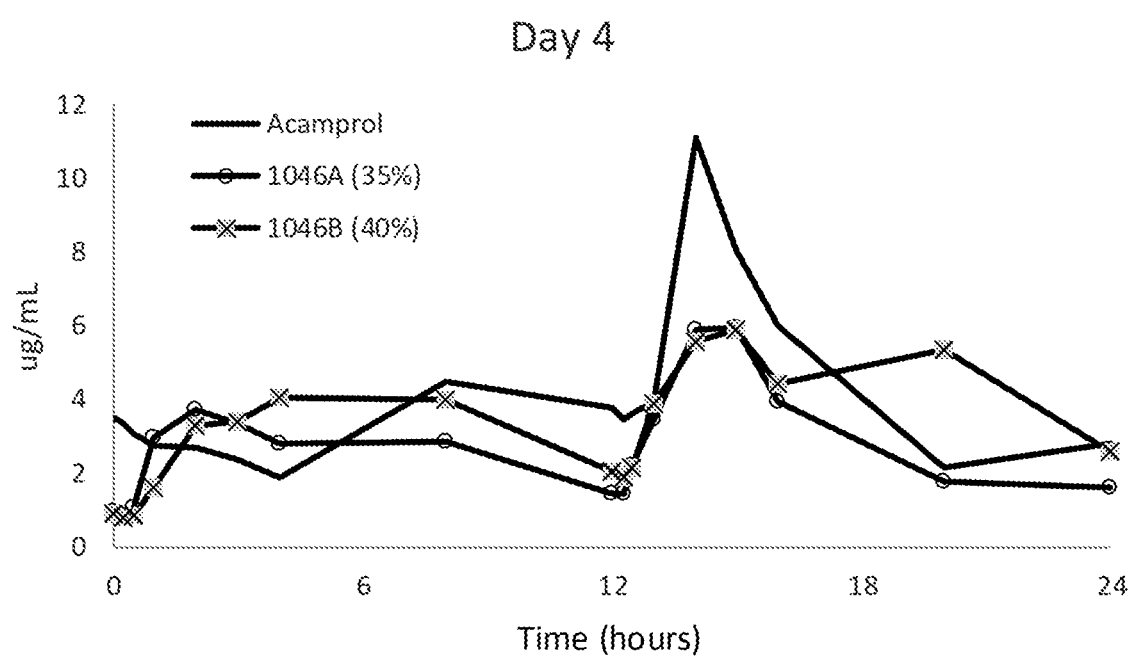
FIG. 4 shows the observed concentration of circulating acamprosate in dogs for formulations described herein compared against a Reference tablet for dosing Day 4. Dosing for each formulation was normalized to 2×333 mg acamprosate calcium, BID for each example.

FIG. 3 and FIG. 4 show that compared to Acamprol tablets (Sun Pharma, BSR 3074), the formulations described herein exhibit a more rapid onset, a more sustained release profile, and more consistent host animal exposure to acamprosate calcium on both Day 1 and Day 4. In contrast, Acamprol showed a more irregular exposure profile with higher peaks and lower troughs.

Reference Examples

Two different marketed enteric-coated tablets were evaluated for dissolution, and the details of the products and dissolution results are presented in the following Tables.

Dissolution of CAMPRAL 333 mg Tablet (A416140) (Reference Example)

| Tablet No. | pH 1.2 (% release) 2 hr | pH 6.8 citrate buffer, Basket, 180 RPM (% release) | | | | |
|---|---|---|---|---|---|---|
|  |  | 30 min | 60 min | 90 min | 120 min | 180 min |
| 1 | 0 | 30 | 73 | 93 | 99 | 99 |
| 2 | 0 | 28 | 67 | 89 | 99 | 99 |
| 3 | 0 | 27 | 62 | 87 | 98 | 98 |
| AVG | 0 | 28 | 67 | 90 | 99 | 99 |
| STDEV | 0.0 | 1.5 | 5.5 | 3.1 | 0.6 | 0.6 |
| RSD | 0 | 5.36 | 8.21 | 3.44 | 0.61 | 0.61 |

Dissolution of ACAMPROL 333 mg Tablet (Reference Example)

| Tablet No. | pH 1.2 (% release) 2 hr | pH 6.8 citrate buffer, Basket, 180 RPM (% release) | | | | |
|---|---|---|---|---|---|---|
|  |  | 30 min | 60 min | 90 min | 120 min | 180 min |
| 1 | 0 | 46 | 70 | 89 | 90 | 91 |
| 2 | 1 | 44 | 63 | 81 | 89 | 95 |
| 3 | 0 | 66 | 87 | 93 | 95 | 96 |
| AVG | 0 | 52 | 73 | 88 | 91 | 94 |
| STDEV | 0.6 | 12.2 | 12.3 | 6.1 | 3.2 | 2.6 |
| RSD | 0.00 | 23.46 | 16.85 | 6.93 | 3.52 | 2.77 |

The dissolution results of the marketed products indicated that negligible or zero drug release occurred in pH 1.2 buffer, and near complete release in pH 6.8 buffer after 180 minutes. A difference was observed in the release profile between the two marketed tablets after 120-180 min.

Comparative Examples

Each Comparative Example is adapted according to PCT international application No. PCT/US2016/030725, and includes a release coating consisting essentially of EC, and without any HPMC.

Dissolution of Comparative Acamprosate Calcium Sprinkles

| Example | SF16001518 | SF16001518 | SF16001880 |
|---|---|---|---|
| Release Coating | 5% (+w)/w EC | 5% (+w)/w EC | 5% (+w)/w EC |
| Enteric Coating | 30% (+w)/w Eudragit coating | 40% (+w)/w Eudragit coating | 50% (+w)/w Eudragit coating |

-continued

| Example | SF16001518 | SF16001518 | SF16001880 |
|---|---|---|---|
| | pH 1.2 | | |
| 2 hr | 22 | 6-11 | 4 |
| | pH 6.8 | | |
| 30 min | 96 | 40-79 | 75 |
| 60 min | 101 | 57-94 | 81 |
| 90 min | 103 | 68-96 | 94 |
| 120 min | 100 | 74-102 | 96 |
| 180 min | 105 | 80-105 | 101 |

The data show that thicker release coatings can mitigate premature release, whereas thin release coatings require thicker enteric coating to ensure minimal release at pH 1.2.

Dissolution of Comparative Acamprosate Calcium Sprinkles

| Example | SF16001518 | SF16001518 | SF16001880 |
|---|---|---|---|
| Release Coating | 10% (+w)/w EC | 10% (+w)/w EC | 10% (+w)/w EC |
| Enteric Coating | 30% (+w)/w Eudragit coating | 40% (+w)/w Eudragit coating | 50% (+w)/w Eudragit coating |
| | pH 1.2 | | |
| 2 hr | 16 | 9 | 6 |
| | pH 6.8 | | |
| 30 min | 57 | 50 | 49 |
| 60 min | 67 | 64 | 62 |
| 90 min | 78 | 71 | 70 |
| 120 min | 83 | 75 | 77 |
| 180 min | 90 | 83 | 85 |

The data also show that thin release coatings exhibit higher overall premature release at pH 1.2, and require thicker enteric coatings. The data also show that thin release coatings exhibit variability during the sustained release at pH 6.8, whereas the thicker release coatings are more consistent regardless of enteric coating thickness.

Dissolution of Comparative Sprinkles on Storage at 40° C./75% RH

| 20% (+w)/w EC; 50% (+w/w) Eudragit coating | | | | |
|---|---|---|---|---|
| Time Interval | Initial | 1 month | 3 months | 6 months |
| Assay (%) | 103.51% | 98.79% | 107.0% | 100.0% |
| Dissolution (average, N = 3) | | | | |
| 120 min (pH 1.2 buffer) | 3 | 3 | 0 | 3 |
| Dissolution in pH 6.8 buffer | | | | |
| 30 min | 44 | 66 | 74 | 88 |
| 60 min | 59 | 79 | 87 | 100 |
| 90 min | 71 | 86 | 95 | 104 |
| 120 min | 77 | 90 | 95 | 106 |
| 180 min | 85 | 94 | 98 | 107 |

Dissolution of Comparative Sprinkles on Storage at 40° C./75% RH

| 5% (+w)/w EC; 50% (+w/w) Eudragit coating | | | | |
|---|---|---|---|---|
| Time Interval | Initial | 1 month | 3 months | 6 months |
| Assay (%) | 97.8 | 99.6 | 99.10 | 98.4 |
| Dissolution (average, N = 3) | | | | |
| 120 min (pH 1.2 buffer) | 4 | 4 | 3 | 3 |
| Dissolution in pH 6.8 buffer | | | | |
| 30 min | 75 | 79 | 75 | 82 |
| 60 min | 81 | 89 | 85 | 93 |
| 90 min | 94 | 88 | 89 | 98 |
| 120 min | 96 | 96 | 91 | 101 |
| 180 min | 101 | 98 | 92 | 103 |

The data also show that release rate for the thicker release coatings, though initially more consistent, changes by as much as 100% after storage. Thus, it becomes a problem to simultaneously optimize the three desired characteristics of near zero release at pH 1.2, consistent sustained release at pH 6.8, and storage stability. It was unexpectedly discovered that release coatings comprising HPMC can be thin, and yet still mitigate premature release at pH 1.2, provide sustained release at pH 6.8, and can be stored with less consequential variability in performance.

What is claimed is:

1. An orally-administrable, pharmaceutical formulation comprising a plurality of pellets, wherein:
    the pellets comprise a core, a release coating, and an enteric coating; and where
    the core comprises acamprosate calcium and a diluent; and the release coating comprises an hydroxypropyl methylcellulose (HPMC); and the enteric coating comprises a polymer of methacrylic acid or a derivative thereof.
2. The pellets of claim 1 wherein the diluent comprises a microcrystalline cellulose (MCC).
3. The pellets of claim 1 wherein the diluent comprises a cellulose gel.
4. The pellets of claim 1 wherein the core comprises about 30% to about 80% acamprosate calcium by weight.
5. The pellets of claim 1 wherein the release coating comprises a thermoplastic cellulose ether other than an ethyl cellulose, or a mixture of one or more thermoplastic cellulose ethers and an ethyl cellulose.
6. The pellets of claim 1 wherein the release coating comprises an HPMC.
7. The pellets of claim 1 wherein the release coating comprises a mixture of HPMC and an ethyl cellulose.
8. The pellets of claim 7 wherein the ratio of HPMC to the ethyl cellulose is about 4.5 to about 0.5 by weight.
9. The pellets of claim 7 wherein the ratio of HPMC to the ethyl cellulose is about 1 or greater by weight.
10. The pellets of claim 1 wherein the enteric coating comprises an anionic polymer.
11. The pellets of claim 1 wherein the enteric coating comprises a polymer or copolymer comprising acrylate radicals or esters thereof, or methacrylate radicals or esters thereof, or a combination of any of the foregoing.
12. The pellets of claim 1 wherein the enteric coating is a copolymer of methacrylic acid and methyl methacrylate radicals.

13. The pellets of claim 12 wherein the ratio of methacrylic acid residues to methyl methacrylate residues is in the range from about 1:3 to about 3.1.

14. The pellets of claim 1 wherein the enteric coating comprises a Eudragit.

15. The pellets of claim 1 comprising about 30% or more acamprosate calcium by weight.

16. The pellets of claim 1 comprising about 0.1% or more HPMC by weight.

17. The pellets of claim 1 comprising about 5% or less of an ethyl cellulose by weight.

18. The pellets of claim 1 comprising about 30% or less anionic polymer by weight.

19. The pellets of claim 1 comprising about 4000 ppm or less total organic solvent.

20. The pellets of claim 19 wherein the organic solvent comprises acetone, or isopropanol, or a combination thereof.

* * * * *